United States Patent [19]
Bewick-Sonntag et al.

[11] Patent Number: 5,762,641
[45] Date of Patent: Jun. 9, 1998

[54] ABSORBENT CORE HAVING IMPROVED FLUID HANDLING PROPERTIES

[75] Inventors: Christopher Phillip Bewick-Sonntag, Kelkheim; Mattias Schmidt, Idstein; Manfred Plischke, Steinbach/Ts., all of Germany

[73] Assignee: The Procter & Gamble Company, Cincinnati, Ohio

[21] Appl. No.: 569,069

[22] PCT Filed: Jun. 27, 1994

[86] PCT No.: PCT/US94/07201

§ 371 Date: Jun. 7, 1996

§ 102(e) Date: Jun. 7, 1996

[87] PCT Pub. No.: WO95/01146

PCT Pub. Date: Jan. 12, 1995

[30] Foreign Application Priority Data

Jun. 30, 1993 [EP] European Pat. Off. .............. 93305150

[51] Int. Cl.[6] ................................................ A61F 13/15
[52] U.S. Cl. ............................................ 604/378; 604/368
[58] Field of Search .......................... 604/378, 368, 604/385.1; 428/283, 284, 286, 288, 290

[56] References Cited

U.S. PATENT DOCUMENTS

| | | | |
|---|---|---|---|
| 4,578,068 | 3/1986 | Kramer et al. | 604/368 |
| 4,600,458 | 7/1986 | Kramer et al. | 156/199 |
| 5,019,063 | 5/1991 | Marsan et al. | 604/378 |
| 5,087,506 | 2/1992 | Palumbo | 428/327 |
| 5,134,007 | 7/1992 | Reising et al. | 604/378 |
| 5,139,841 | 8/1992 | Makoui et al. | 604/378 |
| 5,196,456 | 3/1993 | Nguyen et al. | 522/81 |
| 5,304,161 | 4/1994 | Noel et al. | 604/378 |
| 5,328,935 | 7/1994 | Van Phan et al. | 521/64 |
| 5,387,208 | 2/1995 | Ashton et al. | 604/378 |
| 5,486,167 | 1/1996 | Dragoo et al. | 604/378 |

FOREIGN PATENT DOCUMENTS

| | | |
|---|---|---|
| 90/14815 | 12/1990 | WIPO . |
| 91/11163 | 8/1991 | WIPO . |
| 91/11978 | 8/1991 | WIPO . |
| 92/11831 | 7/1992 | WIPO . |

*Primary Examiner*—John G. Weiss
*Assistant Examiner*—David J. Cho
*Attorney, Agent, or Firm*—Carl J. Roof; E. Kelly Linman; Jacobus C. Rasser

[57] ABSTRACT

An absorbent core comprises, in sequence through it thickness, a first structure comprising an upper layer comprising a first fibrous material having compressibility of at least 5 cm$^3$/g and a drip capacity of a least 10 g/g, the structure also comprising a first superabsorbent material having a substantially non-decreasing dynamic swelling rate and a second a structure comprising a second fibrous material and a second superabsorbent material having a dynamic swelling pressure of at least 15 g/g at 10 g/cm$^2$ (0.7 psi), wherein the dynamic swelling rate of the first superabsorbent material is not greater than ⅔ of the dynamic swelling rate of the second superabsorbent material. The absorbent core allows improved fluid handling of body discharges throughout the core and in the subsequent efficient storage of these discharges.

15 Claims, 6 Drawing Sheets

ABSORBENT CORE HAVING IMPROVED FLUID HANDLING PROPERTIES

This application is a 371 of PCT/US94/07201 filed on Jun. 27, 1994.

BACKGROUND OF THE INVENTION

The present invention relates to an absorbent core for use in articles such as disposable diapers, incontinence articles, sanitary towels, training pants and the like, having improved fluid handling properties.

Typically absorbent articles of this kind comprise a liquid previous topsheet that faces the wearer's body, a liquid impervious backsheet that faces the wearer's clothing, and an absorbent core interposed between the liquid previous topsheet and the liquid impervious backsheet. The absorbent core must be capable of absorbing and handling relatively large volumes of fluid and other exudates discharged from the body of the wearer, and especially relatively large fluid volumes discharged over relatively short periods of time. The absorbent core needs to be capable of acquiring, distributing, and storing discharges initially deposited on the topsheet of the absorbent article. Preferably the design of the absorbent core is such that the core acquires the discharges substantially immediately after they have been deposited on the topsheet of the absorbent article, with the intention that the discharges do not accumulate on or run off the surface of the topsheet, since this may result in inefficient urine containment by the absorbent article which may lead to wetting of outer garments and discomfort for the wearer. In addition, preferably the absorbent core will have a design that facilitates the initially retained discharges to be transported away from the area of initial retention to a place within the core where they can be stored, so that regions of the core do not become prematurely saturated and so that bulk of the absorbent material in the core is utilized effectively.

There have been many attempts to design an absorbent core to satisfy, or improve, the above requirements. For example, WO92/11831 discloses an absorbent article having an absorbent core that comprises a wrapped multi-layer absorbent body comprising at least one acquisition/distribution layer for acquiring body discharges; at least one storage layer positioned subjacent each acquisition layer, and having a further storage layer subjacent the wrapped multi-layer body.

The acquisition/distribution layer comprises a low density web or batt of material that can be fibrous non-woven material. The layer can contain a small amount absorbent gelling material, provided it does not affect its acquisition/distribution properties. The storage layers comprise "high speed" absorbent gelling material, i.e. material that gives a high rate of absorption, and optionally some fibrous material. The gelling material can be particulate, but is preferably fibrous. A preferred embodiment of the wrapped absorbent body comprises two acquisition/distribution layers and two storage layers, and has a pathway, or other type of interconnection, between each pair of layers. The pathway is thought to be necessary to allow body discharges to travel through an upper storage layer that may be subject to "gel blocking" and therefore have a reduced discharge uptake or transportation, to an underlying pair of acquisition/distribution and storage layers. Further pathways tend to be necessary as further storage layers are added.

"Gel blocking" is a phenomenon that tends to interfere with the transportation of fluids in an absorbent structure, by increasing the resistance to fluid flow through that structure. This typically occurs either through swollen superabsorbent particles filling the available inter-fibre void spaces or swollen finer superabsorbent particles blocking capillary (transport) channels thereby restricting the transport of fluid.

The absorbent article disclosed in WO92/11831 has the disadvantage that it is a relatively complex structure because of the need to provide pathways between the upper storage layers and the layers underlying those storage layers. Despite the provision of the pathways between the layers there may still be a tendency in some instances, particularly when relatively high basis capacities are desired, for gel blocking to occur in some areas of the absorbent article, thereby reducing the effective utilization of absorbent capacity in the article.

WO91/11163 discloses an absorbent structure having a fluid acquisition/distribution layer comprising chemically stiffened cellulosic fibres, and optionally a very small amount (no more than about 6%) of superabsorbent material; and a fluid storage layer, subjacent the acquisition/distribution layer, comprising at least 15% superabsorbent material. A disadvantage with the disclosed absorbent structure is that fluid flow through the structure in the Z-direction can be hindered, and therefore inadequate, as a result of gel blocking, leading to under-utilization of absorbent capacity. This tends to become particularly problematic when using smaller and thinner structures requiring relatively high basis capacities (or high concentrations of superabsorbing material).

WO91/11978 discloses an absorbent body for use in diapers or similar articles. The disclosed absorbent body comprises a first layer of airfelt or other conventional fibre fluff mixed with a first superabsorbent material having a high degree of cross-linking, and a second layer which contains a second superabsorbent material having a higher liquid absorbency than the first superabsorbent material. When the fluff in the first layer becomes wet it tends to collapse under the weight of the absorbed liquid and under the pressure exerted on it by external loads. The highly cross-linked superabsorbent material present in the first layer attempts to prevent total collapse of the fluff, allowing it to maintain, and perhaps regain after collapse, void volume so that it can again absorb subsequent liquid discharges.

The disadvantage with the absorbent body disclosed in WO91/11978 is that the control of fluid transfer from the first layer to the second layer tends to be poor which tends to result in saturation of the upper layer prior to the lower layer thereby leading to under-utilization of absorbent capacity.

WO90/14815 discloses a disposable absorbent article that includes at least two superabsorbent materials that differ with regard to their absorption properties and their liquid retention abilities as defined in that disclosure. It is preferred that the absorbent article disclosed comprises a superabsorbent with a high retention ability in an upper layer and a superabsorbent with a high absorption rate in a lower layer, the two layers being separated by distance maintaining dispersion layers, such as a tissue or non-woven layer.

The absorbent article disclosed has poor fluid absorption properties, and one result of this is that the article tends to exhibit only a limited ability to remove and store body fluids away from the user's skin; this phenomenon is generally referred to as poor rewet tendency. In addition, the structure tends to have substantial deficiencies in fluid acquisition and distribution within the structure which leads to inefficient or under-utilization of core absorbent capacity.

SUMMARY OF THE INVENTION

The present invention is intended to improve upon some of the problems of the prior art with regard to the fluid handling and absorption properties.

According to the invention an absorbent core comprises, in sequence through its thickness,

- a first structure comprising an upper layer comprising a first fibrous material having a wet compressibility of at least about 5 cm$^3$ g$^{-1}$ and a drip capacity of at least 10 g$^{-1}$, the structure also comprising a first superabsorbent material having a substantially non-decreasing dynamic swelling rate and
- a second structure comprising a second fibrous material and a second superabsorbent material having a dynamic swelling rate of at least about 0.2 g$^{-1}$ s$^{-1}$ and an absorption against pressure of at least about 15 g g$^{-1}$ at 50 g cm$^{-2}$ (0.7 psi),
- wherein the dynamic swelling rate of the first superabsorbent material is not greater than ⅔ of the dynamic swelling rate of the second superabsorbent material.

The tests referred to above, and other tests mentioned herein, are described in more detail below.

The absorbent core may be manufactured by cutting to shape from a continuous length of material or it may be formed initially in situ (i.e. laid down as a core) in a mold of the desired shape according to well known manufacturing techniques as detailed below. The first structure is intended to be positioned towards a wearer's body in use.

The absorbent core of the invention has the advantage that it allows improved flow control or fluid handling of body discharges throughout the core and in the subsequent efficient storage of these discharges.

The design of the absorbent core of the invention is thought to allow saturation of the core first in the region of the core furthest away from the wearer's body, and then gradually closer to the wearer's body until the core has reached its maximum capacity. The invention achieves this by providing a first structure as described above which acts initially as an acquisition/distribution structure and that is relatively permeable to body discharges. The discharges therefore pass relatively quickly through the first structure into the second structure where the discharges are preferentially stored. In addition, the superabsorbent material in the first structure acts to dry out the fibrous material in that structure, and since the first structure is for positioning adjacent the wearer's body, skin dryness is improved.

The second structure has properties that allow it to effectively influence the flow of discharges through the first structure. This second structure has the ability to do this since it has faster absorption kinetics than the first structure.

In order to achieve the essential and preferred performance characteristics it is necessary to select appropriate combinations of various materials in the cores, as well as their amounts. The following description refers to suitable materials and by subjecting appropriate test articles made from them to the specified tests, and modifying the articles when necessary to achieve the required test results, cores according to the invention are achieved.

For instance to achieve the above described fluid handling advantages the first structure should be sufficiently open, or permeable, relative to the second structure to allow quick passage of body discharges through the first structure and into the second structure. However, the first structure should not be too open as this could lead to a higher risk of gel-blocking of the superabsorbent material in the second structure, thereby under-utilizing the absorbent capacity in that structure. A balance should be struck. The defined parameters of wet compressibility, drip capacity, dynamic swelling rate and absorption against pressure achieve the desired results.

The upper effective layer of the core (excluding any tissue or topsheet if present) comprises fibrous material of the defined wet compressibility and the defined drip capacity. The fibrous material therefore maintains its openness, or void volume, when wetted by, for example, urine. The provision of such a permanently open fibrous layer having a high drip capacity in the core means that not only does the core acquire body discharges, such as urine, rapidly, but that it also has the potential to transfer these discharges into the subjacent structure of first particulate superabsorbent material relatively quickly.

The first fibrous material can be any fibrous material that has a suitable resistance to load when wet, i.e. is able to maintain satisfactory void volume under such conditions. This will be called in the following "the wet compressibility" of the fibrous material. Wet compressibility is measured by the Wet Compressibility Test described below.

The "wet compressibility", or void volume per gram of fibrous material under a 77.5 gcm$^{-2}$ (1.1 psi) load, of the first fibrous material is at least 5 cm$^3$g$^{-1}$, preferably at least 6 cm$^3$g$^{-1}$, and most preferably at least 6.5 cm$^3$g$^{-1}$.

The first fibrous material preferably has a "drip capacity" of at least 10 mlg$^{-1}$, preferably at least 15 mlg$^{-1}$, and most preferably at least 20 mlg$^{-1}$. The "drip capacity" is a measure of the ability of a fibre matrix to receive synthetic urine at a loading point, transfer it away from that point and then hold it within the matrix. The "drip capacity" is measured by the Drip Capacity Test described below.

The first structure can comprise first particulate superabsorbent mixed with the first fibrous material as a substantially homogeneous upper layer, but preferably some (and preferably substantially all) of the superabsorbent is present in a distinct layer below the upper layer of first fibrous material.

The second, or storage-structure can comprise a mixture of the second fibrous material and the second superabsorbent material. Preferably, however, they are present in distinct layers.

In a preferred embodiment of the invention each of the first and second structures comprises a layer of its respective fibrous material separate from a layer of its respective superabsorbent material. The preferred embodiment of the core of the invention therefore comprises in sequence from the side of the core adjacent the wearer's body in use a layer comprising the first fibrous material, layer comprising the first particulate superabsorbent material, a layer comprising the second fibrous material and a layer comprising the second superabsorbent material.

There can be a tissue layer interspersed between each layer of the core, which acts as a containment barrier for the superabsorbent material.

Suitable first fibrous material can comprise chemically stiffened cellulosic fibres. Preferred chemically stiffened cellulosic fibres are stiffened, twisted, curled cellulosic fibres which can be produced by internally cross-linking cellulose fibres with a cross-linking agent. The types of stiffened, twisted, curled cellulosic fibres useful as the hydrophillic fibre material of the absorbent structures described herein are described in greater detail in the following patents: U.S. Pat. No. 4,882,453 entitled "Absorbent Structure Containing Individualized Cross-linked Fibres", issued to Dean et al. on Apr. 18, 1989; U.S. Pat. No. 4,888,093 entitled "Individualized, Cross-linked Fibres And Process For Making Said Fibres", issued to Dean et al. on Dec. 19, 1989; U.S. Pat. No. 4,889,595 entitled "Process For Making Individualized, Cross-linked Fibres Having Reduced Residuals And Fibres Thereof", issued to Herron et al. on Dec. 26, 1989; U.S. Pat. No. 4,889,596 entitled "Process for Making Individualized Cross-linked Fibres and Thereof", issued to Schoggen et al. on Dec. 26, 1989; U.S. Pat. No. 4,889,597 entitled "Process For Making Wet-Laid Structures Containing Individualized Stiffened Fibres", issued to Bourbon et al. on Dec. 26, 1989; and U.S. Pat. No. 4,898,642 entitled "Twisted, Chemically Stiffened Cellulosic Fibres And Absorbent Structures Made Therefrom", issued to Moore et al. on Feb. 5, 1990.

Mixtures of synthetic and natural fibres can be used such as polyethylene, polypropylene, viscose and rayon fibres, and bi-component fibres of these materials, mixed with airfelt, cellulose, modified cellulose (as above) or other natural fibres. Typically such a mixture will have at least about 5% synthetic fibres, and preferably at least about 10% synthetic fibres.

The first fibrous material layer is generally formed by air laying the desired fibres during the production of the absorbent core as detailed below, but if desired a preformed non-woven or other fibrous material can be used.

The first superabsorbent material allows body discharges that are rapidly acquired by the first fibrous material layer to pass into the first superabsorbent material layer and to be distributed beyond this layer into the subjacent core structure. Body discharges not so distributed will ultimately be stored in the first superabsorbent material layer.

A suitable superabsorbent material for use in the first structure must have a substantially non-decreasing dynamic swelling rate. The dynamic swelling rate of a superabsorbent material is a measure of the uniaxial swelling of the superabsorbent material in a test tube as synthetic urine is added to it as a function of time. The test method used to measure the dynamic swelling rate is called the Dynamic Swelling Rate Test, and is described below.

The second structure may promote further lateral distribution of the body discharges before these enter the second superabsorbent material. The fibrous material of this second structure can add an extra stage of control to the absorption profile of the absorbent material of the invention. For instance it may slow down the passage of body discharges as they leave the first structure superabsorbent layer and prior to them reaching the second superabsorbent layer material when, as is preferred, this is in an underlayer. This may minimize the chances of gel-blocking occurring in the second superabsorbent material, which due to its faster absorption kinetics tends to be more sensitive to this phenomenon.

The second fibrous material may comprise fibrous material of any conventional type. The fibrous material can be airfelt, a mixture of natural and synthetic fibres, chemically cross-linked cellulose fibre or any other known fibrous material commonly used in absorbent cores of absorbent articles. If desired it may include some fibres of the same type as the first fibrous material.

Each fibrous layer may add integrity and may also add softness to the absorbent core.

The second superabsorbent material must have faster absorption kinetics than the first superabsorbent material. As a result it absorbs body discharges faster than the first superabsorbent material and, provided the first structure remains sufficiently permeable, results in body discharges being drawn from the first structure into its own structure.

In order to achieve the required control in the flow of body discharges within the core of the invention the second superabsorbent material necessarily has a dynamic swelling rate of at least 0.2 grams urine per second per gram of superabsorbent material ($g\ g^{-1}\ s^{-1}$). Preferably the dynamic swelling rate of the second superabsorbent material is at least 0.3 $g\ g^{-1}\ s^{-1}$. The dynamic swelling rate is measured according to the Dynamic Swelling Rate Test described below.

The ability of the second superabsorbent material to effectively influence the flow of body discharges from the upper layers of the absorbent core and to provide adequate storage under typical in use conditions is measured in terms of the absorption of synthetic urine by the superabsorbent material against a defined pressure. This is measured by the Absorption Against Pressure Test described below.

The second superabsorbent material has an absorption against pressure of at least 15 g synthetic urine per g of superabsorbent material ($g\ g^{-1}$), and preferably at least 20 g $g^{-1}$, at 50 g $cm^{-1}$ (0.7 psi) pressure.

In order to sustain the permeability of the first structure on successive loadings of the core, to ensure the desired fluid handling properties, the absorption kinetics of the second superabsorbent material must be faster than those of the first superabsorbent material. This is measured in terms of the dynamic swelling rate of each of the superabsorbent materials, wherein the dynamic swelling rate of the first superabsorbent material is not greater than ⅔, and preferably not greater than ⅓, of that of the second superabsorbent material.

The first and second superabsorbent materials may be of any suitable physical shape, e.g. fibrous, film or particulate. Preferred materials are particles that may be true spheres, granules, aggregates, agglomerates or irregular shaped particles as typically produced by a grinding process. Typically they are hydrogel-forming polymers which comprise an acrylate polymer or copolymer.

Examples of superabsorbent materials having the above described properties are AQUALIE CA® (available from Nippon Shokubai Co. Ltd., Osaka, Japan) and FAVDR SX® (available from Chemische Fabrik Stockhausem GmbH, Krefeld, Germany).

When, as is preferred, the superabsorbent material is present as a layer separate from the first and second fibrous material, the superabsorbent layer can include fibrous material of any of the known kinds, but preferably each such layer consists substantially entirely of the respective superabsorbent material in that no deliberate addition of non-superabsorbent fibres is made to it.

The particulate superabsorbent material can be substantially entirely polymeric absorbent hydrogel-forming material, or can comprise a mixture of superabsorbent hydrogel-forming material with an additive, such as for example, powdered silica.

When, as is preferred the superabsorbent material is present as a separate layer the distribution within that layer can be varied, for example to provide a shaped design which may be striped, see for example EP-A-217,666, or profiled within the layer, see for example U.S. Pat. No. 4,935,022. Alternatively, the layer may be profiled in the Z-direction either gradually or in the form of distinct sub-layers, see for example EP-A-198,683 and EP-A-478,011.

Another consequence of having a separate superabsorbent layer is that the superabsorbent material can be introduced as a preformed layer, thereby simplifying the manufacturing process. Such preformed layers typically consist of super-absorbent material integrated with or dispersed within a support medium, such as a cellulose-based tissue or other non-woven material. The preformed layers can be made by mechanical means such as embossing or calendering. Alternatively, the preformed layers can consist of substantially pure superabsorbent material in the form of sheets or film-like structures. Such sheets or films can be formed during polymerisation of the superabsorbent material, or by bonding together particles or fibres of superabsorbent material by adhesives or other suitable means. For example U.S.

Pat. No. 5,102,597 and U.S. Pat. No. 5,124,188 describe processes of producing sheets of bonded particulate superabsorbent material.

The required difference in superabsorbent absorption kinetics can be achieved by providing superabsorbent materials having different particle sizes or physical shape in the first and second storage layers. In which case, the first storage layer mainly comprises coarser material, and the second storage layer mainly comprises finer material.

The use of coarse particles in the first structure promotes permeability. Finer particles have a larger surface to volume ratio than coarser particles, and therefore may be capable of faster absorption than coarser particles, provided there is no gel blocking. Confining the finer absorbent material to the second structure also has the advantage of reducing the risk of its escape onto the skin of the wearer and also reducing the risk of pock-marking which can be caused by the particulate superabsorbent material penetrating the impervious backsheet.

The particle size of the superabsorbent material is expressed as a median mass particle size. This is measured by the Sieve Test described below. The median mass particle size of the coarse superabsorbent material of the first structure is preferably more than 300 µm (50 mesh), more preferably in the range of 400 to 850 µm (20 to 40 mesh), and most preferably in the range of 600 to 850 µm (20 to 30 mesh). The finer material of the second structure typically has a median mass particle size of less than 300 µm (50 mesh) but above 50 µm (325 mesh), preferably in the range of 100 to 250 µm (60 to 140 mesh), and more preferably in the range of 150 to 250 µm (60 to 100 mesh).

An alternative to using superabsorbent materials of different particle sizes to provide the required difference in absorption kinetics between the first and second storage layers is to use different chemical types of superabsorbent material having inherently different absorption speeds. The superabsorbent materials can be different chemical composition, for example cross-linked partly neutralized polyacrylic acid or a starch-based superabsorbent material. Alternatively, they can be different by virtue of their production processes, for example, a "broken-gel process" or an inverse suspension (or bead) polymerisation.

Another way in which the superabsorbent materials may differ chemically is that they may be cross-linked with different cross-linking agents or to different extents, or one of the superabsorbent materials may be surface cross-linked, or they both may be surface cross-linked to different extents. Examples of such cross-linked superabsorbent materials have been given above.

The absorbent core of the invention has improved fluid handling properties over the prior art, and therefore its incorporation into an absorption article provides improved performance of the article. In addition, the design of the core allows the absorbent articles to be made relatively small and thin, i.e. compact, while maintaining this improved performance. The absorbent core of the invention has an average theoretical basis capacity of at least 0.7 ml cm$^{-2}$, preferably at least 0.8 ml cm$^{-2}$.

The average theoretical basis capacity is calculated by summing the basis capacities of the individual components to get the theoretical basis capacity of the core, and then taking the average. The basis capacity is termed theoretical because for its calculation it requires that the total capacity be broken down into the individual capacities, and also because it is a measurement carried out in the absence of any applied load; the core is often under load in natural use. In calculating the average theoretical basis capacity, the basis capacity of the superabsorbent material is calculated assuming the "Teabag" capacity. The "Teabag" capacity is measured by the Teabag Retention Capacity Test described below.

The absorptive capacity of each of the fibrous materials is measured by the X,Y-Demand Absorbency Test described below. In this test airfelt typically absorbs about 4 g synthetic urine per gram of dry fibres, and chemically cross-linked cellulose as described in U.S. Pat. No. 4,898,642, for example, typically absorbs about 6 g synthetic urine per gram of dry fibres at a pressure of 20 g cm$^{-2}$ (0.3 psi).

The absorbent core of the invention can be made relatively thin and yet have high absorbency. This is considered beneficial to the user in terms of, for example the fit of the article in which the core is incorporated and its discretion in use, as well as for manufacturing reasons, for example cost minimization of packaging and transportation. Preferably the stack height or caliper of the core of the invention as measured at 200 gcm$^{-2}$ (3 psi) (unless otherwise stated) in a stack height test, described below, is not more than 9 mm, and is preferably not more than about 7.5 mm. The stack height test is a method for assessing the packaging potential of a stack of 10 diapers. Typically the test is conducted to determine the level of compression, or force, needed to compress a diaper stack during manufacture to a thickness required by packaging dimensions. It can also be used to determine what pressure (in g cm$^{-2}$) such a stack would exert on the package material.

An absorbent article comprising the absorbent core of the invention generally has a caliper that is substantially the same as the caliper of the absorbent core, and is usually not more than 10%, for example, above the caliper of the core. The absorbent article can be made to a greater caliper, by for example incorporating additional absorbent fibrous, for example tissue, or other material on one or both sides of the core, but unless the material is selected carefully this may detract from the performance of the absorbent core.

The absorbent core preferably has an acquisition rate of at least 1.5 ml s$^{-1}$ at 50% of the theoretical basis capacity. Since the absorbent core of the invention comprises in different regions superabsorbent materials having different absorption kinetics, the fluid acquisition profile of the core may vary from point to point both in the XY plane and in the Z-direction, and will vary during acquisition. It is therefore thought more realistic to measure the acquisition rate at 50% of the total theoretical capacity (rather than at the unused or fully used conditions). This allows an average in-use core performance assessment to be expressed in the acquisition rate measurement.

The acquisition test simulates the introduction of urine into an absorbent article. The test measures the time an absorbent article, for example a diaper, needs to absorb a certain load of synthetic urine. It is measured by the Acquisition Rate Test described below.

In addition to a good fluid acquisition, the absorbent core of the invention preferably has good fluid uptake properties. The core preferably has a fluid uptake rate of at least 0.05 grams urine per second per gram dry material (g g$^{-1}$ s$^{-1}$), and preferably more than 0.06 g g$^{-1}$ s$^{-1}$. Fluid uptake is a measure of the efficiency of the absorbent core structure to absorb fluid and then readily distribute it. It is measured by the X,Y-Demand Absorbency Test described below.

A further consequence of the fluid handling and absorption properties of the absorbent core of the invention is apparent from its good rewet properties. The absorbent core the invention has a rewet of no greater than 0.6 g synthetic urine, preferably no greater than 0.3 g, and most preferably no greater than 0.2 g. A low rewet value indicates a high, or efficient, urine retention by the absorbent core, or the absorbent article in which it is incorporated. A high rewet indicates poor urine retention, which may lead to accumulation of urine on the surface of the core or article thereby causing rewetting of the user's garments and/or the user itself. Rewet is measured by the Rewet Test described below.

The absorbent core of the invention can comprise in some or all of its layers tissue laminates or other nonwoven structures (which can have superabsorbent material included in them) provided that these do not detract from the performance of the material.

The core of the invention can be made by air laying, or by wet laying, the appropriate materials (fibres and superabsorbent) in sequence in conventional manner, or by assembling preformed layers, for example of the superabsorbent materials as described above, or by any suitable combination thereof. For example, GB-A-2,191,793 and GB-A-2,191,515 describe methods of air laying fibrous materials using a rotating drum laydown system, and GB-A-2,175,024 and EP-A-330,675 describe the incorporation of superabsorbent material into the absorbent structures.

According to a further aspect of the invention an absorbent article comprises a liquid previous topsheet, a liquid impervious backsheet, and an absorbent core as described above interposed between the topsheet and the backsheet with the first structure positioned towards the topsheet and the backsheet is positioned towards the second structure.

The article may be, for instance, a sanitary napkin but is preferably an incontinence article, a training pant or a disposable diaper. It may be constructed in a conventional manner. For instance the backsheet may be secured to the absorbent core by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The adhesive preferably comprises an open pattern network of filaments of adhesive as is disclosed in U.S. Pat. No. 4,573,986 entitled "Disposable Waste-Containment Garment", which issued to Minetola et a. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et a. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet is substantially impervious to liquids (e.g., urine) and is preferably manufactured from a thin plastic film, although other flexible liquid impervious materials may also be used. The backsheet prevents exudates absorbed and contained in the core from wetting articles which contact the absorbent article such as bedsheets and undergarments. The backsheet may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mil). Particularly preferred materials for the backsheet include RR8220 blown films and RR5475 cast films as manufactured by Tredegar Industries, Inc. of Terre Haute, Ind. The backsheet is preferably embossed and/or matte finished to provide a more clothlike appearance. Further, the backsheet may permit vapours to escape from the absorbent core (i.e., breathable) while still preventing exudates from passing through the backsheet.

The topsheet is positioned adjacent the body surface of the absorbent core and is preferably joined thereto and to the backsheet by attachment means such as those well known in the art. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the article is a diaper wherein topsheet and the backsheet are joined directly to each other in the diaper periphery and elsewhere are indirectly joined by directly joining them to the absorbent core.

The topsheet is compliant, soft feeling, and non-irritating to the wearer's skin. Further, the topsheet is liauid previous permitting liquids (e.g., urine) to readily penetrate through its thickness. A suitable topsheet may be of natural and synthetic fibres. Preferably, the topsheet is made of a material that is hydrophobic to isolate the wearer's skin from liquids contained in the absorbent core. There are a number of manufacturing techniques which may be used to manufacture the topsheet. For example, the topsheet may be a nonwoven web of fibres spunbonded, carded, wet-laid, meltblown, hydroentangled, combinations of the above, or the like. A preferred topsheet is carded and thermally bonded by means well known to those skilled in the fabrics art. A preferred topsheet comprises a web of staple length polypropylene fibres such as SAWABOND® (trade name) manufactured by Sandler GmbH & Co. KG, Schwarzenbach, Germany.

BRIEF DESCRIPTION OF THE DRAWINGS

The invention is now further described by way of reference to the following drawings:

FIGS. 2 to 7 inclusive are referred to in the Test Methods, and are described therein.

DETAILED DESCRIPTION OF THE INVENTION

Figure 1A:
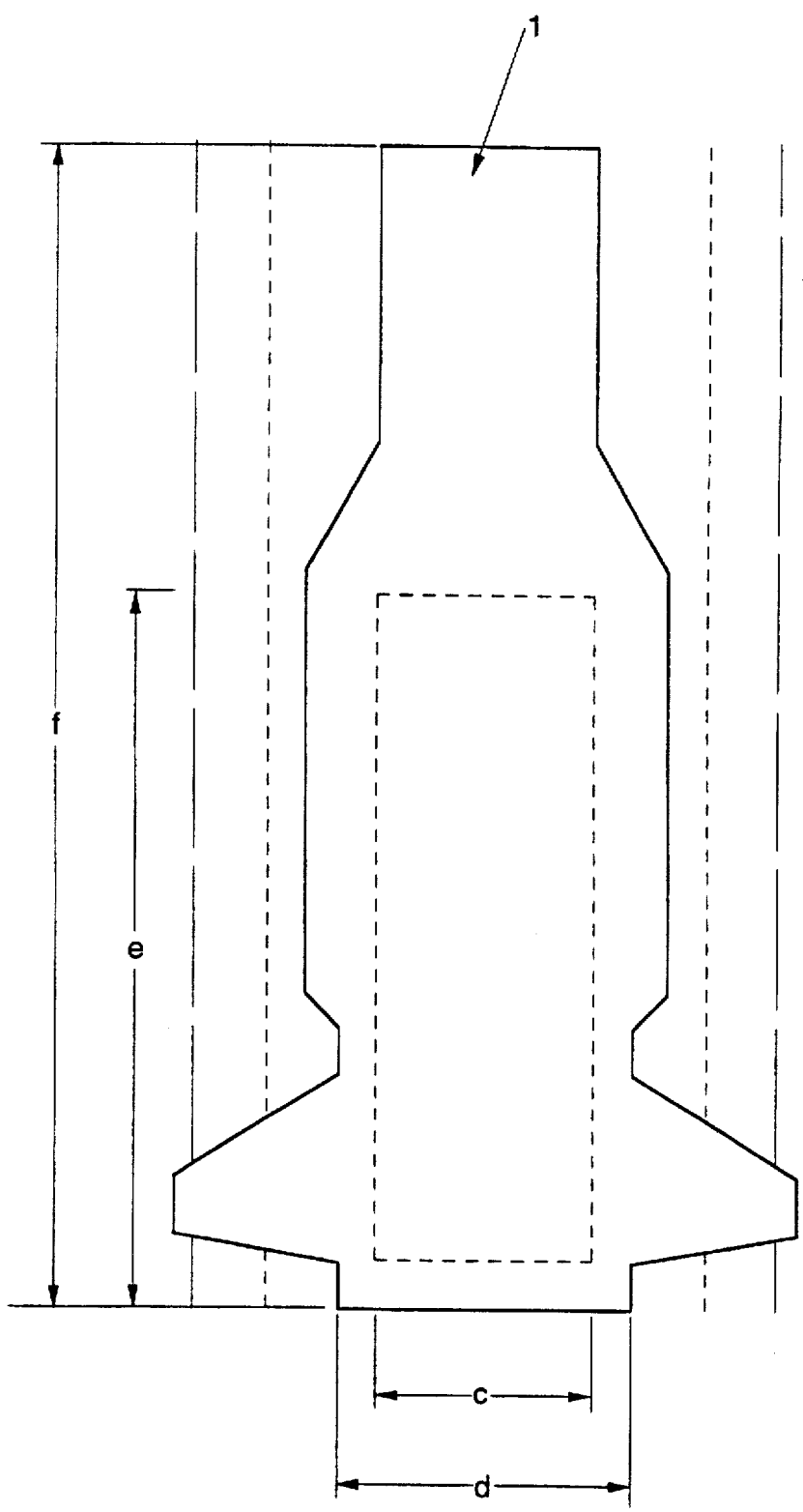
FIG. 1a is a diagrammatic plan view of an absorbent article according to the present invention.

Referring to FIGS. 1a, b and c, the article 1 comprises a top sheet 2 which contacts the body of the wearer, a backsheet 9 and the novel core between the topsheet and backsheet. The core comprises the first acquisition/distribution layer 3 comprising the first fibrous material having a wet compressibility and drip capacity as defined. A tissue layer 4 having two folds in the z-direction separates the first acquisition layer 4 from the first superabsorbent layer 5 comprising superabsorbent material having relatively slow absorption kinetics. Below this is the second acquisition/distribution layer 6, and below this a second superabsorbent layer 7 comprising superabsorbent material having relatively fast absorption kinetics. The lower surface of the second storage layer 7 is bound by a second tissue layer 8. Other elements of the diaper, such as crotch, waistband and fastening features are not shown.

In a typical diaper for a baby in the weight range 9–18 kg width c is about 7.6 cm (3"), width d is about 10.2 cm (4"), length e is about 25.5 cm (10"), and length f is about 40 cm (15.7").

EXAMPLES

Figure 1B:
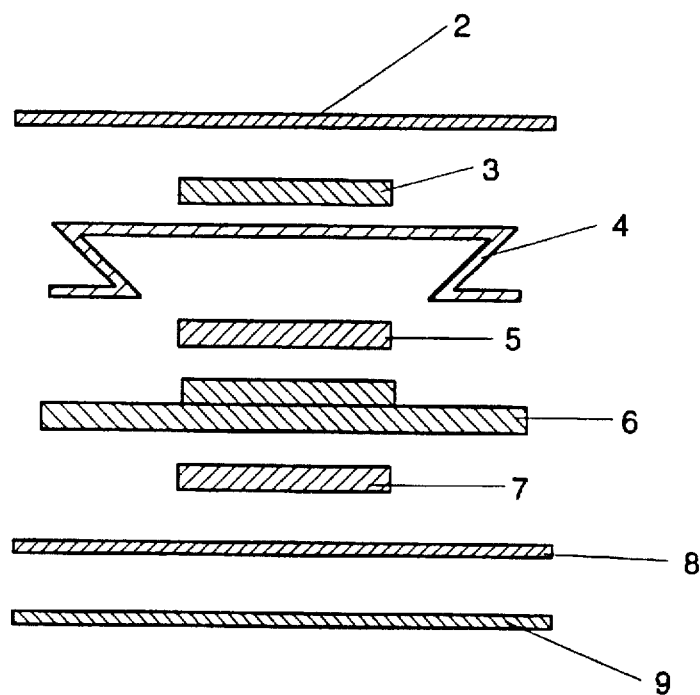
FIG. 1b is a diagrammatic cross-sectional view showing the layer structure of the article in the cross direction.
Figure 1C:
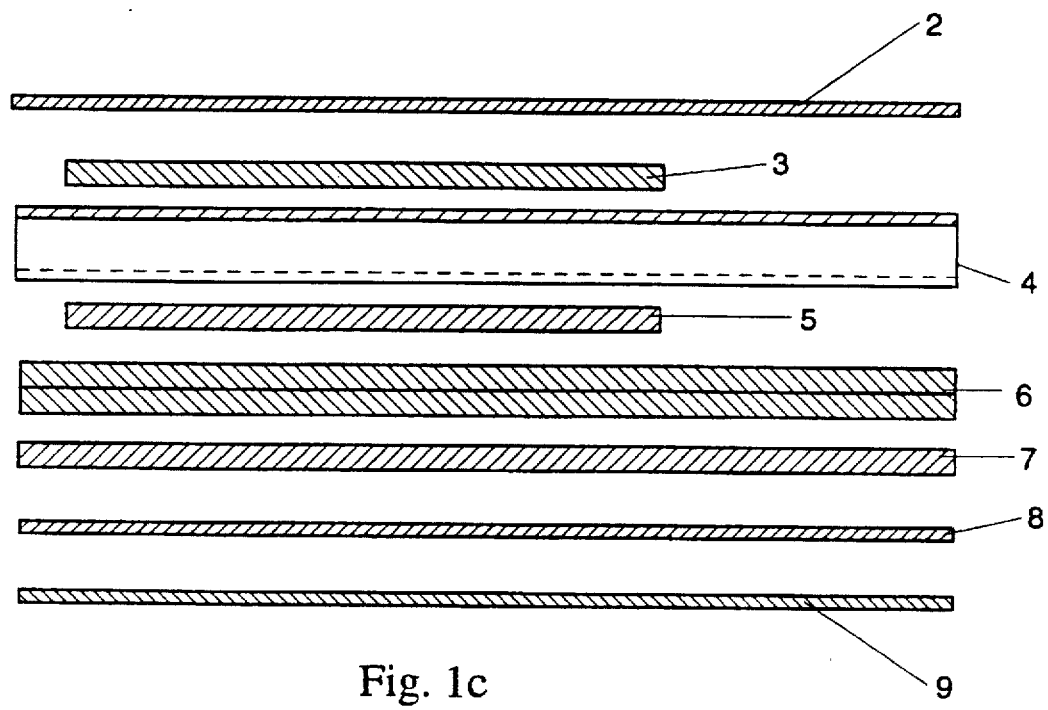
FIG. 1c is a diagrammatic article cross-sectional in the length direction.

Examples 1–3 are examples of cores constructed in accordance with the invention and as shown in FIGS. 1a to 1c.

Example 1 is an absorbent core according to the invention having a high basis capacity.

Example 2 is an absorbent core according to the invention having a medium basis capacity.

Example 3 is an absorbent core according to the invention having the low basis capacity.

Table 1 illustrates the layer structure of Examples 1 to 3 and gives the properties of those respective cores.

The performance of the three examples of the invention was compared against a number of different structures, including two of the applicants' commercial structures and a commercial structure of another major absorbent article manufacturer. The results are illustrated in Table 2.

Comparative Example 1 is an absorbent article having a core comprising airfelt only and including a topsheet and a backsheet.

Comparative Example 2 is an absorbent article having a core comprising only chemically cross-linked cellulose as described above, and including a topsheet and a backsheet.

Comparative Example 3 is an absorbent article marketed under the trade name PAMPERS BABY DRY® [(Boy Maxi Size (8–18 kg)]. This product comprises a mixed airfelt/superabsorbent core, having a patch of the same chemically cross-linked material as in comparative Example 2 located on top.

Comparative Example 4 is an absorbent article marketed under the trade name Pampers Phases. This product has a mixed airfelt/superabsorbent core.

Comparative Example 5 is an absorbent article that is marketed under the trade name ULTRATRIM® [Boy Size 4 (10–16 kg)] by the Kimberley Clark Corporation. This product has a core that is an airfelt/superabsorbent mix.

Comparative Example 6 is an absorbent article made according to WO92/11831 and having a structure substantially identical to that of Example 2 but having a different superabsorbent material. The first and second (having double the basis weight of the first) superabsorbent materials are very "high-speed" gelling materials and comprise NOR-SOLOR® X50 superabsorbent material (supplied by ELF

TABLE 1

| Design | Core Weight[1] (g) | Core Area (g) | Fibre Weight[2] (g) | Fibre Capacity (ml) | Super-absorbent Weight (g) | Super-absorbent Capacity (ml) | Total Core (ml) | Theoretical Basis Capacity (ml cm$^{-2}$) |
|---|---|---|---|---|---|---|---|---|
| Example | | | | | | | | |
| 1 | 31 | 213 | 10.5 | 33.00 | 15.00 | 465.00 | 498.00 | 2.34 |
| 2 | 27 | 213 | 12.5 | 37.50 | 9.80 | 295.00 | 332.50 | 1.56 |
| 3 | 31 | 337 | 14.3 | 34.00 | 8.50 | 264.00 | 298.00 | 0.89 |

[1]Core weight includes topsheet, containment tissue and core covering impervious backsheet.
[2]Total weight of all core fibres excluding tissue.

| Design | 1st Acquisition Layer Material Basis Weight (gm$^{-2}$) Dimensions | 1st Superabsorbent Layer Material Basis Weight (gm$^{-2}$) Dimensions | 2nd Acquisition Layer Material Basis Weight (gm$^{-2}$) Dimensions | 2nd Superabsorbent Layer Material Basis Weight (gm$^{-2}$) Dimensions |
|---|---|---|---|---|
| Example | | | | |
| 1 | CCLC[3] 294 25 cm × 7.5 cm | SXM-W 20/30[4] 267 25 cm × 7.5 cm | CCLC 294 25 cm × 7.5 cm | SXM-W 60/100[4] 533 25 cm × 7.5 cm |
| 2 | CCLC 294 25 cm × 8.5 cm | SXM 300[5] 160 25 cm × 7.5 cm | CCLC 294 25 cm × 7.5 cm | SXM-W 60/100[4] 320 25 cm × 7.5 cm |
| 3 | CCLC 280 25 cm × 7.5 cm | L761f20/30[6] 100 25 cm × 7.5 cm | CCLC 280 45 cm × 7.5 cm | L761f60/100[6] 240 45 cm × 7.5 cm |

[3]CCLC is chemically cross-linked cellulose as described in US 4,898,642, for example.
[4]SXM-W is superabsorbent produced under the trade name FAVOR SX, sieved to the listed particle size in mesh, i.e., 20/30 mesh (600 to 850 μm), 600/100 mesh (150 to 250 μm).
[5]SXM 300 is superabsorbent produced under the trade name FAVOR SX used as bulk (unsieved).
[6]L761f is superabsorbent produced under the trade name AQUALIC CA, sieved to the listed particle size in mesh, i.e., 20/30 mesh (600 to 850 μm), 600/100 mesh (150 to 250 μm).

ATOCHEM, Cedex, France). The first superabsorbent layer is 7.5 cm wide and has a 0.5 cm superabsorbent free stripe along each of its longitudinal sides, as described in WO92/11831.

Comparative Example 7 is an absorbent article made according to WO90/14815 and having a structure similar to that of Example 2 but having a tissue having a basis weight of 60 gm$^{-2}$ instead of CCLC as the second acquisition layer and having different superabsorbent materials. The first and second (having double the basis weight of the first) superabsorbent materials have different absorption rates and liquid retention abilities, and comprise respectively AQUALIC CA W-4® (supplied by Nippon Shokubai Co. Ltd., Osaka, Japan) and SANWET IM 56005® (supplied by Hoechst-Casella GmbH, Frankfurt, Germany).

Unless otherwise specified each of the topsheet and the backsheet used in the Examples and Comparative Examples is of the type described above.

The important parameters reflecting the advantages of the invention over the prior art, as represented by the comparative examples, are summarised in Table 2. Each parameter listed in that table represents only one specific benefit of the core of the invention to the user of an article incorporating the core, either throughout the article's lifetime or during a particular phase of its lifetime. The core of the invention exhibits good performance in a majority of the listed parameters, as compared with the comparative examples. More specifically the core of the invention generally exhibits:

1) A good acquisition rate (at least 1.0 ml s$^{-1}$) at 50% average theoretical basis capacity, which reflects good fluid absorption throughout the core's, and therefore the article's, in use lifetime;

2) A high $X_{90}/t_{90}$ (at least 0.05 g g$^{-1}$ s$^{-1}$) as measured by the X, Y-demand absorbency test, which indicates an efficient distribution mechanism within the core leading to efficient utilization of storage capacity.

TABLE 2

| Design | Design Structure | | | |
|---|---|---|---|---|
| | Core Weight (g) | Core Area (cm$^2$) | Theoretical Basis Capacity (ml cm$^{-2}$) | Pressure to achieve stack height of 9.00 mm [gcm$^{-2}$ (psi)] |
| Example | | | | |
| 1 | 31 | 213 | 2.34 | ≦200 (3) |
| 2 | 27 | 213 | 1.54 | ≦200 (3) |
| 3 | 21 | 337 | 0.89 | ≦200 (3) |
| Comparative Example | | | | |
| 1 | 44 | 800 | 0.20 | ≧350 (5) |
| 2 | 11 | 270 | 0.28 | ≦200 (3) |
| 3 | 37 | 750 | 0.45 | ≧350 (5) |
| 4 | 50 | 800 | 0.40 | ≧350 (5) |
| 5 | 40 | 600 | 0.67 | ≦200 (3) |
| 6 | 27 | 213 | 1.54 | ≦200 (3) |
| 7 | 22 | 213 | | ≦200 (3) |

| Design | Performance X, Y-Demand Absorbency | | | | |
|---|---|---|---|---|---|
| | Acquisition Rate at 50 gcm$^{-2}$ (0.7 psi) at 50% Th. Cap. (ml s$^{-1}$) | $X_{90}$ (g g$^{-1}$) | $T_{90}$ (s) | $X_{90}/T_{90}$ (g g$^{-1}$ s$^{-1}$) | Rewet at 50 gcm$^{-3}$ (0.7 psi) at 75% Th(.g)Cap.) |
| Example | | | | | |
| 1 | 1.0 | 17.0 | 300 | 0.060 | 0.25 |
| 2 | 1.8 | 13.0 | 94 | 0.140 | 0.15 |
| 3 | 1.5 | 14.5 | 270 | 0.054 | 0.50 |
| Comparative Example | | | | | |
| 1 | 1.2* | 4.0 | 35 | 0.120 | 10 |
| 2 | 6.9 | 6.7 | 15 | 0.045 | 17 |
| 3 | 1.3 | 14.2 | 410 | 0.035 | 0.20 |
| 4 | 0.82* | 12.8 | 610 | 0.022 | 0.70 |
| 5 | 0.46* | 15.6 | 820 | 0.019 | 0.80 |
| 6 | 1.3 | 16.7 | 225 | 0.075 | 0.70 |
| 7 | 0.62 | 18.6 | 1014 | 0.018 | 10.2 |

*at 25 g cm$^{-2}$ (0.35 psi)

A good core will ideally combine good performance and good design structure. It is generally not acceptable to provide a core having excellent performance, but which is very bulky and therefore not aesthetically pleasing, and which is also expensive to make and/or package.

3) A low rewet (no greater than 0.6 g synthetic urine), which reflects superior skin dryness benefits for the user; and 4) A high average theoretical basis weight (at least 0.8 g g cm$^{-2}$) together with a low stack height (no greater than 9 mm), which allow the production of smaller and thinner efficient absorbent cores, and therefore articles, which are discrete in use, and which also save on packaging and transportation costs.

Only Example 6 of the comparative examples is satisfactory over most of the range of parameters. However Example 2 is a substantially identical structure to this comparative example and has superior performance to it with respect to both acquisition rate, rewet, and X, Y-demand absorbency properties, without the manufacturing complexities that tend to be required by the structure of Comparative Example 6 (as exemplified by the passages or pathways from upper storage layers to lower layers within the core structure). The superiority of the core of the invention in respect of these parameters is thought to be a result of a combination of the different fluid uptake rates of the superabsorbent materials together with their inclusion in the specific structure of the core of the invention.

Test Methods

All tests are carried out at about 23 ±2° C. and at 50±10% relative humidity.

The specific synthetic urine used in the test methods is commonly known as Jayco SynUrine and is available from Jayco Pharmaceuticals Company of Camp Hill, Pa. The formula for the synthetic urine is: 2.0 g/: of KCl; 2.0 g/l of $Na_2SO_4$; 0.85 g/l of $(NH_4)H_2PO_4$; 0.15 g/l $(NH_4)H_2PO_4$; 0.19 g/l of $CaCl_2$; ad 0.23 g/l of $MgCl_2$. All of the chemicals are of reagent grade. The pH of the synthetic Urine is in the range of 6.0 to 6.4.

Sample Pad Preparation for Wet Compressibility and Drip Capacity Tests

The sample pads are prepared using a padmaker machine, such as is described below or an equivalent machine, which provides a consistent and homogeneous laydown of fluff.

Figure 3:
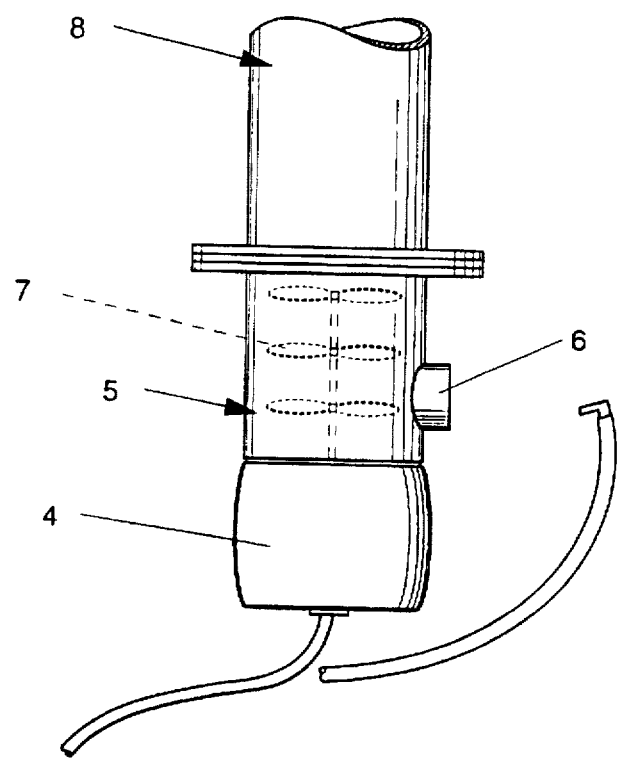
FIG. 3 is an enlarged view of a portion of FIG. 2.
Figure 2:
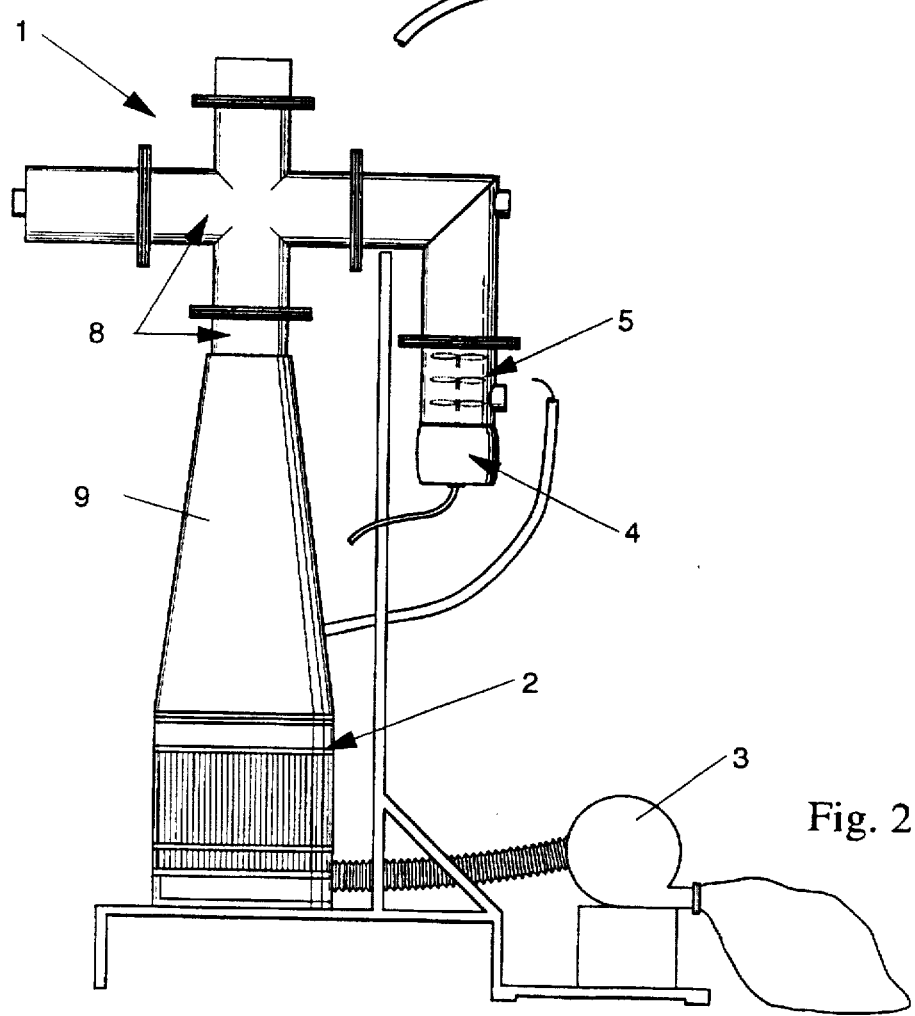
FIG. 2 is a side view of an air laid felt padmaker machine used to make the sample pads for the Wet Compressibility and Drip Capacity Tests.

Referring to FIGS. 2 and 3.

Four 30 g portions of dry fluff (or equivalent material, for example chemically cross-linked cellulose) are weighed out. A ply of tissue porous enough for air to pass through it while retaining fluff on it, is cut to 36.8 cm×36.8 cm (14.5"×14.5"), and is placed evenly on the forming screen (2) of an air laid felt padmaker machine (1). The tissue (not shown) completely covers the forming screen and is made to curve up at its sides to prevent escape of the fluff. The tissue forms the bottom of the pad.

The vacuum (2), chamber motor (4) and compressed air supply on the padmaker machine are turned on. One 30 g portion of fluff is added to the sample chamber (5) on the padmaker machine in small amounts via the sample feed (6) and without obstructing the blades (7) of the machine. Compressed air is circulated vigorously in the chamber to expedite separation and passage of the fibres through the plexiglass cylinder (8) and the prismoid column (9) to the forming screen (2).

The vacuum (3) is turned off and the forming screen (2) is pulled out of the padmaker machine (1) and rotated through a quarter turn in the clockwise direction. The screen is returned to the padmaker machine. Another 30 g portion of fluff is added to the chamber (5) on the machine and the above procedure is repeated. Fluff is added in the same manner until all four portions have been transferred to the forming screen. The forming screen, and the pad formed thereon, is then removed from the padmaker machine, and the pad is carefully transferred from the screen to a piece of cardboard, or similar smooth flat surface. A second ply of tissue is added to the top of the pad, and a second piece of cardboard placed on top of that.

A steel weight having dimensions of around 35.6 cm×35.6 cm×2.5 cm (14"×14"×1) having a weight of around 16.3 kg (36 lbs) is placed on top of the pad for approximately 120 seconds, or longer until the pad is needed. The weight is then removed and the pad is pressed by application of a force of around 4,500 kg (10,000 lbs) on a large Carver press to improve pad integrity. The pad is removed from the press and trimmed on a paper cutter to have dimensions around 30.5 cm×30.5 cm (12"×12"), and is then further cut according to the size required by the particular test in which it is to be used.

The use of a padmaker machine to form the sanmle pads is not intended to be limiting. Any suitable method can be used provided a consistent and homogeneous laydown of fluff is achieved, which is then compressed under the above conditions to give a pad having substantially the same density and basis weight as achieved above.

Wet Compressibility Test

This test is designed to measure the volume of a pad of fibrous material under varying load conditions when wet. The objective is to measure the fibrous material's resistance to load by measuring the volume maintained under that load.

A fluff test pad is prepared as described above. Any tissue present on the surfaces of the pad is removed. The pad is then densified under a 3.6 kg $cm^{-2}$ (51 psi) load for pad integrity reasons using a Carver laboratory press. The thickness of the pad is measured and its fibre density calculated by pad weight÷(pad thickness×pad area).

The dry weight of the pad is multiplied by 10, and this represents the target wet weight on loading. The dry pad is transferred onto a top loading balance having a 0.01 g sensitivity. Synthetic urine is dispensed slowly onto the pad until the target wet weight is achieved as measured by the balance. The wet pad is carefully transferred onto the surface of a compressibility tester of the Buckeye design, and a weight having substantially the same area as the pad (about 10.2 cm×10.2 cm) and corresponding to a pressure of 77 g $cm^{-2}$ (1.1 psi) is lowered slowly onto the pad. The pad is left for 60 seconds to allow it to equilibrate under the load, and then the thickness of the compressed pad is recorded using calipers.

The Wet Compressibility is the void volume per gram of dry fluff and is calculated as follows:

Void Volume $(cm^3)$=Total Volume–Fiber Volume=(pad thickness under load $(cm^3)$×pad area $(cm^2)$)–(pad dry weight (g)/fibre density (g $cm^3$)

Wet Compressibility=Void volume per gram=[(pad thickness underload (cm)×pad $(cm^2)$)–(pad dry wt. (g)/fibre density (g $cm^{-3}$)]÷pad dry wt. (g)

where fibre density is calculated from the initial pad weight and thickness measurements (i.e. under no load conditions).

Drip Capacity Test

A sample pad prepared as described above is cut on a paper cutter to have dimensions 7.5 cm×7.5 cm. The pad is weighed and is placed on a large mesh wire screen which is in turn positioned on a drip tray. The whole apparatus is then mounted on a top-loading balance.

Synthetic urine is introduced via a pump (Model 7520-00, as supplied by Cole-Parmer Instruments Company, Chicago, USA) into the centre of the sample pad at a rate of 5±0.25 ml $s^{-1}$. The time for the pad to release the first drop of synthetic urine through the bottom of the pad and into the drip tray is recorded. The pump is immediately stopped as soon as this occurs. The time recorded and the pumping rate are then used to calculate the volume (ml) of synthetic urine absorbed by the sample on reaching saturation, i.e. when the sample starts to drip. (The balance can be used to check this periodically, thereby minimizing any variation in the pump delivering the synthetic urine. This is known as the Drip Capacity, and is given as the ratio:

Urine retained by sample pad on saturation (ml)/Dry Weight of sample (g)

Dynamic Swelling Rate Test 0.358 g, to the nearest 0.001 g, of dry superabsorbent material is placed in a standard test tube having an outer diameter of 16 mm, a height of 125 mm and a wall thickness of 0.8 mm, which is supported to be a vertical, for example by placing in a test tube stand. (Only previously unused test tubes should be used in this test, and should be discarded after use).

10 ml Jayco synthetic urine is added to the test tube using an automatic pipette at a rate of about 5 ml s$^{-1}$. As the synthetic urine is added the superabsorbent material begins to swell, forming a front that moves upwards in the test tube. The height of the front is recorded as a function of time, either manually or using an image analyser after video recording. The height of the front is then translated into momentary X-load, X(t)-load, of synthetic urine per gram dry superabsorbent material, wherein $$X(t) = \frac{h(t) \times 28}{H},$$

where h(t) is the length of the swollen superabsorbent material up the test tube at time t, and H is the total height of synthetic urine in the tube that would correspond to a total X-load of 28 (10 g synthetic urine absorbed by 0.358 g superabsorbent gives a X-load of 28); the X-load being the weight in grams of synthetic urine that 1 gram of dry of superabsorbent material can absorb.

The X(t)-load is then plotted against time. It is assumed that the equilibrium absorbent capacity of the superabsorbent material under test is greater than 28 g g$^{-1}$.

The ratio of the X(t)-load to the time t at which it is measured is called the "Swelling Rate Function" (SR) and is the average swelling rate in achieving X(t), i.e.

$$SR(t) = \frac{X(t)}{t}.$$

In the context of this application the "Dynamic Swelling Rate" (DSR) is the value of the swelling rate function when X(t) is 28 gg$^{-1}$, i.e.

$$DSR = \frac{28gg^{-1}}{t_{28}},$$

where $t_{28}$ is the time to reach of X(t)=28 g g$^{-1}$.

For the purpose of this application the dynamic swelling rate test is interpreted as follows. If no gel blocking occurs at the front of the superabsorbent material the material can be said to be relatively permeable and the graph of X(t) against time will be a substantially horizontal line. This means that the function SR(t) is substantially constant.

Alternatively, with some materials permeability increases during swelling, in which case SR(t) increases with increasing time, also showing the absence of gel blocking. If gel blocking occurs, however, permeability decreases during swelling SR(t) decreases with increasing time.

In the context of this application a superabsorbent material is said to have a substantially non-decreasing dynamic swelling rate if the swelling rate function does not decrease substantially between the two times $t_{14}$ (the time when the superabsorbent material is swollen to 50%, i.e. where X(t) =14 g g$^{-1}$) and $t_{28}$, as defined above. That means the relative deviation [SR($t_{14}$)−SR ($t_{28}$)]÷SR ($t_{28}$) of the swelling rates at $t_{14}$ and $t_{28}$, is less than 50%, preferably less than 25%, more preferably less than 10% or most preferably less than or equal to 0%.

Absorption Against Pressure Test

This test measures the absorptive capacity of a superabsorbent material absorbing against an external pressure of 20 g cm$^{-2}$ (0.3 psi), in terms of the uniaxial swelling of the superabsorbent material against that pressure.

A ceramic filter plate having a diameter of 120 mm and 0 porosity (ceramic filter DURAN® from Schott) is placed in a petridish having a diameter of 150 mm and a height of 30 mm. 0.9% by weight sodium chloride solution in distilled water is added to the Petri dish so that the filter plate is covered. A round filter paper having a diameter of 125 mm (SCHWARZBAND 589® from Schleicher and Schull) is placed on the filter plate and is thoroughly wetted with the sodium chloride solution.

A Plexiglass cylinder having an inner diameter of 60 mm +/−0.1 mm and a height of 50 mm, is closed at its bottom with a screen filter cloth having apertures of a diameter of 36 μm (400 mesh). 0.9000 g +/−0.0005 g of superabsorbent material is carefully scattered onto the filter screen of a clean and dry Plexiglass cylinder, as described. It is necessary to obtain a homogeneous distribution of superabsorbent material on the mesh.

A cover plate having an outer diameter of 59 mm +/−0.1 mm, an inner diameter of 51 mm and the height of 25 mm, having an attached weight having a diameter of 50 mm and a height of 34 mm, has a total weight of 565 g, which correspond to a pressure of 20 g cm$^{-2}$ (0.3 psi). The cover plate and weights are placed in the cylinder and the complete cylinder apparatus is weighed on a balance to the nearest 0.01 g. The complete cylinder apparatus is then placed on the wetted filter paper in the Petri dish, and is allowed to absorb for 1 hour. The cylinder apparatus is then removed from the filter plate and is re-weighed.

The cylinder apparatus and filter plate should be cleaned thoroughly between measurements, and the sodium chloride solution and filter paper should be renewed after each measurement.

The absorption against pressure (AAP is calculated as follows:

AAP=[(weight of cylinder apparatus after absorption)−(weight of cylinder apparatus when dry)]÷(initial weight of superabsorbent material).

Sieve Test

The particle size distribution of superabsorbent material is determined by placing a known weight of a sample in a Retsch mechanical sieving device, and shaking for a specified period of time under defined conditions. Sample sections is retained on each sieve and the bottom pan are weighed and reported as percentages of the original sample weight.

100 g +/−0.5 g of dry superabsorbent polymeric material is weighed into a sample cup which is then closed by a lid.

Four sieves are nested from bottom to top as follows: stainless steel bottom pan, No. 325, No. 100, No. 50 and No. 20; these being numbers of the U.S. sieve series (ASTM-E-11-61). The sample is transferred to the upper most of the series of sieves, and the powder is distributed evenly around the screen. A stainless steel cover is placed on the No. 20 sieve.

The nested sieves are placed in position on a Retsch testing sieve shaker VIBOTRONIC TYPE VE1® with timer. It is ensured that the Retsch lid fits as tightly as possible against the top of the shaker. The timer is set for 10 minutes, and started to begin the test. When the shaker has stopped, the nest of sieves is removed from the shaker.

Each of the sieve fractions retained by the sieve is then weighed, for example by different measurements, to the nearest 0.0 g.

It is important to work quickly in this test to avoid moisture pickup by the superabsorbent material.

Teabag Retention Capacity Test

The superabsorbent material is placed within a "teabag", immersed in a synthetic urine solution for 20 minutes, and then centrifuged for 3 minutes. The ratio of the retained liquid weight to the initial weight of the dry superabsorbent material is the absorptive capacity of the superabsorbent material.

21 of 0.9% by weight sodium chloride in distilled water is poured into a tray having dimensions 24 cm×30 cm×5 cm. The liquid filling height should be about 3 cm.

The teabag pouch has dimensions 6.5 cm×6.5 cm and is available from a company called Teekanne in Dusseldorf, Germany. The pouch is heat sealable with a standard kitchen plastic bag sealing device (e.g. VACUPACK$_2$ PLUS® from Krups, Germany).

The teabag is opened by carefully cutting it partially, and is then weighed. A 0.200 g +/−0.005 g sample of the superabsorbent material is placed in the teabag. The teabag is then closed with a heat sealer. This is called the sample teabag.

An empty teabag is sealed and used as a blank.

Each teabag is then held horizontally, and the sample teabag is shaken so as to distribute the superabsorbent material evenly throughout the bag. The sample teabag and the blank teabag are then laid on the surface of the synthetic urine, and submerged for about 5 seconds using a spatular to allow complete wetting (the teabags will float on the surface of the synthetic urine but are completely wetted). The timer is started immediately.

After 20 minutes soaking time the sample teabag and the blank teabag are removed from the synthetic urine, and placed in a BAUKNECHT WS130®, BOSCH 772 NZK096® or equivalent centrifuge (230 mm diameter), so that each bag sticks to the outer wall of the centrifuge basket. [This can be arranged, for example, by folding an end of the teabag in the direction of the centrifuge spin to absorb the initial force?] The centrifuge lid is closed, the centrifuge is started, and the speed increased quickly to 1,400 rpm. Once the centrifuge has been stabilised at 1,400 rpm the timer is started. After 3 minutes, the centrifuge is stopped.

The sample teabag and the blank teabag are removed and weighed separately.

The absorptive capacity (AC) for the sample of superabsorbent hydrogel-forming material is calculated as follows:

AC=[(sample teabag weight after centrifuging)−(blank teabag weight after centrifuging)(dry superabsorbent hydrogel-forming material weight)]÷(dry superabsorbent material weight).

Stack Height Test

The stack height is designed to test the packaging potential of a stack of 10 absorbent articles, e.g. diapers, to simulate in-pack conditions.

Ten absorbent articles, or absorbent cores according to this invention assembled into a chassis including a topsheet (as described above) and a backsheet (as described above) to simulate a finished product deliverable to the market, are typically folded at the centre (doubled over) to conform to package width and length dimensions. The stack of 10 articles is precompressed in a hydraulic press (THWING-ALBERT INSTRUMENT COMPANY, MODEL TA 240-10, ALPHA HYDRAULIC PRESS/SAMPLE CUTTER, PHILADELPHIA, U.S.A.) under a load of 800 kg for 3 seconds. The precompressed structures are then placed in an Instron Series 6000 tension-compression testing device, available from Instron Ltd. (Bucks, U.K.), and a compression curve is recorded. The compression curve plots the stack height, or caliper of the sample stack, as a function of the exerted compression force. The force is readily converted to determine the pressure required to achieve a given caliper.

The "stack height" is the height or caliper (under a given pressure) of a single article and is determined by averaging the height measured in the stack height test by the number of articles in the stack.

Acquisition Rate Test

Figure 4:
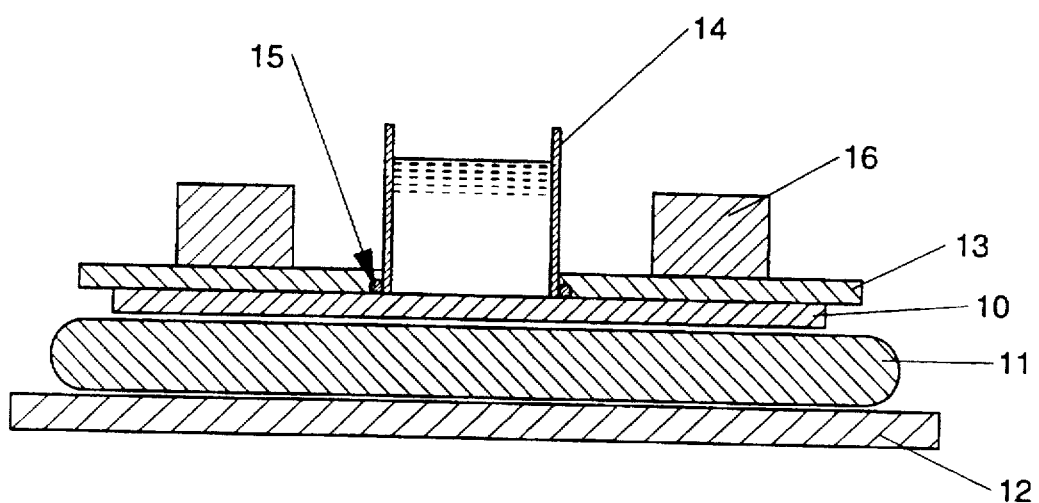
FIG. 4 is a cross-sectional view of the apparatus used in the Fluid Acquisition Test.

Referring to FIG. 4, an absorbent structure (10) is loaded with a 50 ml gush of synthetic urine at a rate of 10 ml s$^{-1}$ using a pump (Model 7520-00, supplied by Cole Parmer Instruments Co., Chicago, U.S.A.), from a height of 5 cm above the sample surface. The time to absorb the urine is recorded by a timer. The gush is repeated every 5 minutes at precisely 5 minute gush intervals until the theoretical capacity is reached.

The test sample, which comprises a core and includes a topsheet (as described above) and a backsheet (as described above), is arranged to lie flat on a foam platform 11 within a perspex box (only the base 12 of which is shown). A perspex plate 13 having a 5 cm diameter opening substantially in its middle is placed on top of the sample. Synthetic urine is introduced to the sample through a cylinder 14 fitted, and glued into the opening. Electrodes 15 are located on the lowest surface of the plate, in contact with the surface of the absorbent structure 10. The electrodes are connected to the timer. Loads 16 are placed on top of the plate to simulate, for example a baby's weight. A pressure of 50 g cm$^{-2}$ (0.7 psi) is typically utilized in this test.

As urine is introduced into the cylinder it typically builds up on top of the absorbent structure thereby completing an electrical circuit between the electrodes. This starts the timer. The timer is stopped when the absorbent structure has absorbed the gush of urine, and the electrical contact between the electrodes is broken.

The acquisition rate is defined as the gush volume absorbed (ml) per unit time (s). The acquisition rate is calculated for each gush introduced into the sample.

As mentioned above, it is considered beneficial in respect of the absorbent core of the invention to determine the acquisition rate on loading to 50% of the theoretical capacity. To determine this point one can either plot the acquisition rate as a function of the total volume of synthetic urine added, and then determine the acquisition rate on absorption to 50% of the theoretical capacity. Alternatively, one can determine it directly by taking the acquisition rate for the nearest gush if this lies within 15 ml of the middle value.

X,Y-Demand Absorbency Test

The X,Y-demand absorbency test method consists of a version of a standard demand wettability test. For reference, standard demand absorbency tests are described in Chatterjee, P. K. (Ed.) Absorbency, Chapter II, pp. 60–62, Elsevier Science Publisher B. V., Amsterdam, The Netherlands (1985).

Figure 6:
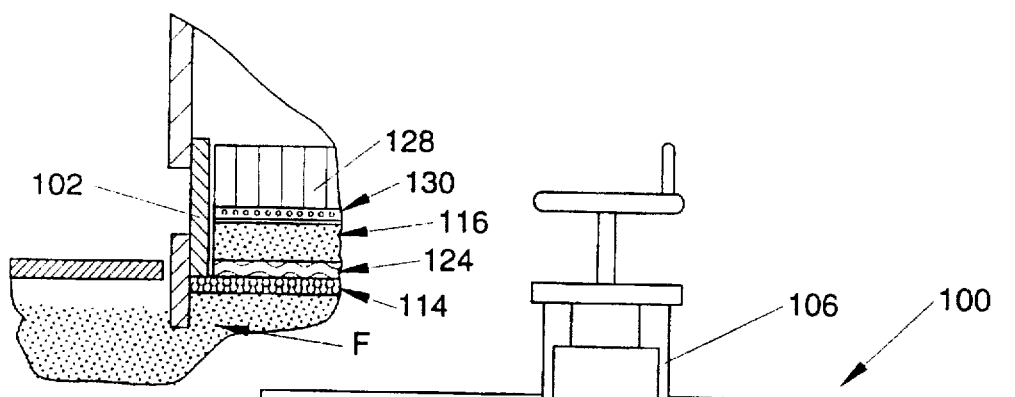
FIG. 6 is an enlarged view of a portion of FIG. 4.
Figure 5:
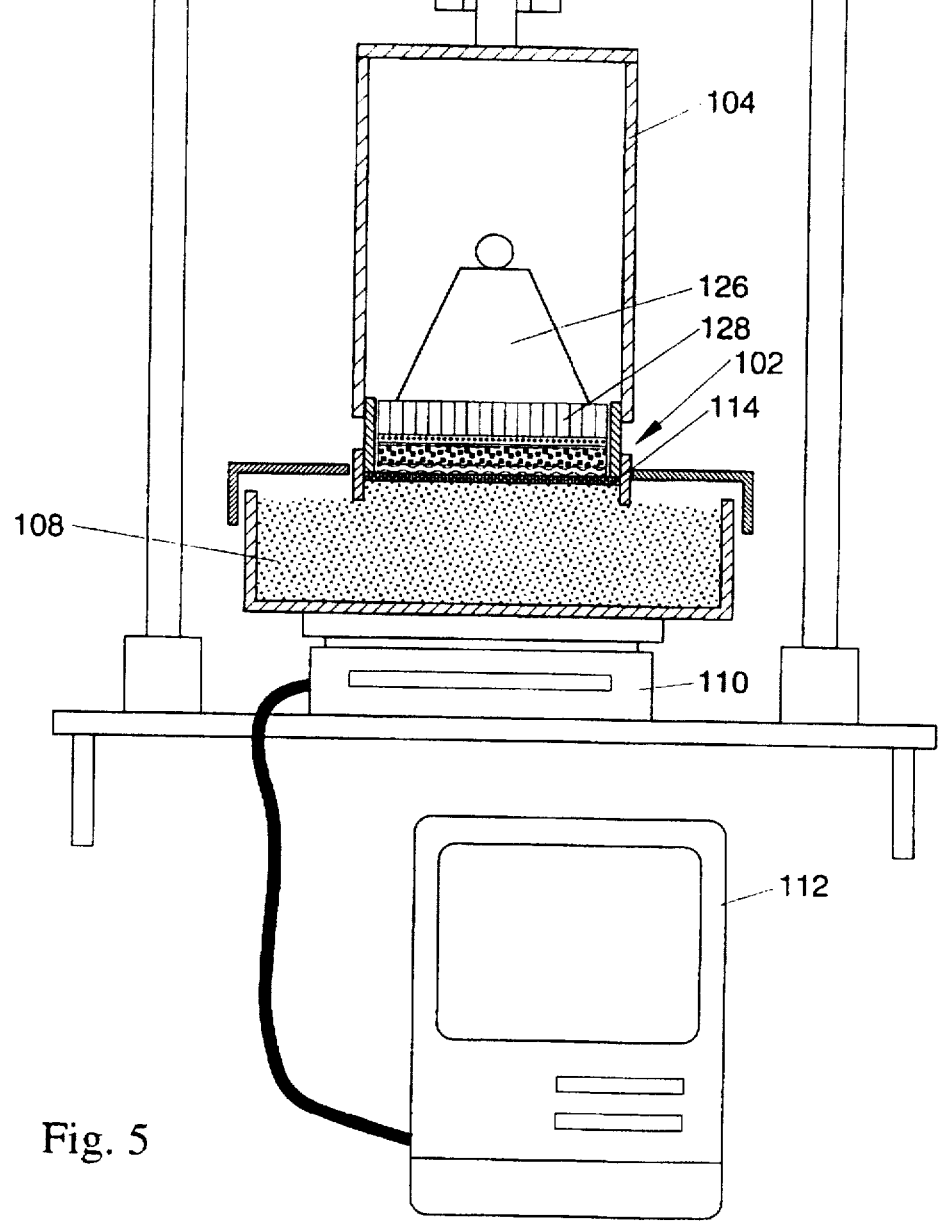
FIG. 5 is a part sectioned side view of apparatus used in the X,Y-Demand Absorbency Test.

The apparatus used to conduct this test is shown in FIGS. 5 and 6. The apparatus 100 consists of a square sample basket 102 suspended on a frame 104. The inside dimensions of the basket are 10.2 cm×7.6 cm (4"×3"). The height of the basket 102 is adjustable via a gear mechanism 106. A fluid reservoir 108 is placed on an electronic balance 110 connected to a computer 112.

Figure 7:
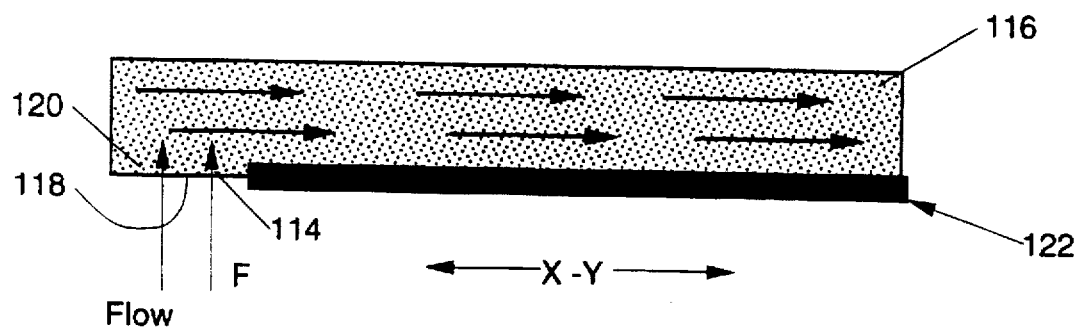
FIG. 7 is a cross-sectional view of liquid flowing in the X-Y plane in an absorbent core according to the invention.

The x-y plane test is shown schematically in FIG. 7. In the x-y plane test, the screen 114 is only present in a 2.54 cm×7.62 cm (1"×3") area 118 along one edge 120 of the sample basket bottom. The remainder of the sample basket bottom, designated 122, is made of Plexiglas and is fluid impervious. The sides of the sample basket that are in contact with the sample are also made of Plexiglas and are fluid impervious. As shown in FIG. 7, this test requires the sample 116, comprising a core and including a topsheet (as described above) and a backsheet (as described above), to first demand the fluid in the z-direction, and then transport it a maximum of 7.62 cm (3") in the horizontal (x-y) plane. The results from the x-y plane test provide a measurement of the sample's ability to distribute fluid under potential in-use conditions. The x-y plane test is carried out with the absorbent structure sample 116 confined under a 20 g cm$^{-2}$ (0.3 psi) load applied evenly to the upper surface of the sample 116.

The test procedure is as follows. First, a 10.2 cm×7.6 cm (4"×3") sample of an absorbent core of the invention is prepared. The fluid reservoir 108 is filled with about 6800 ml of synthetic urine and set on an electronic balance 110 under the test apparatus 100. Then the sample basket 102 is lowered until the fluid level is just at the level near the tope of the wire screen 114. A piece of commercial available 2-ply BOUNTY® paper towel 124 is placed on the wire screen 114 in the bottom of the basket 102. The BOUNTY® towel 124 ensures that consistent fluid contact with the underside of the core sample 116 is maintained throughout the duration of the test.

The applied weight 126 is attached to a square metal plate 128 with dimensions slightly smaller than the inner dimensions of the sample basket 102. Then the top side of the core sample 116 is attached to the bottom of the above-mentioned plate 128 via double sided tape 130, or spray adhesive. At time=zero, the sample 116 is placed into the sample basket 102.

The test is run over a duration of 2000 seconds. At 2000 seconds the final X-Y load, $X_{end}$, is determined by balance measurement (corrected for any evaporation loss over this period)+dry weight of sample. From $X_{end}$ the X-Y load at 90% of this value, $X_{90}$, is calculated, and the corresponding time, $t_{90}$, determined. The fluid uptake rate is defined as the ratio $X_{90}/t_{90}$.

Absorptive Capacity of Fibrous Material by the X,Y-Demand Absorbency Test

The test is carried out identical to that described above except that the sample consists of fibrous material only. In this instance the fibre capacity is $X_{end}$ as opposed to $X_{90}$.

Rewet Test

This test is particularly important with regard to determining the in-use performance of an absorbent core, or an absorbent article in which such a core is incorporated. The test is based upon the measurement of the wetting of a stack of filter papers placed on top of an absorbent core that is loaded with synthetic urine and then placed under a load.

An absorbent core including a topsheet (as described above) and a backsheet (as described above) is laid out flat on a smooth surface with the topsheet uppermost. A volume of synthetic urine equal to 75% of the theoretical basis capacity, calculated as described above, is added at a rate of 7 ml s$^{-1}$ to the absorbent core at a loading point centrally located with regard to the width of the core and approximately 11 cm from the front core edge.

A weight having dimensions 10.2 cm×10.2 cm corresponding to a load of 50 g cm$^{-2}$ (0.7 psi) is placed centrally over the loading point and the core is allowed to equilibrate for 15 minutes under this load. The weight is then removed and 5 layers of pre-weighed filter paper (Eaton Dikeman 939, Nr 7) having dimensions of 10.2 cm×10.2 cm are placed rough side down centrally over the loading point, and the weight is reapplied for 30 seconds. The weight is then removed and the filter papers are weighed. The difference in filter paper weight is the first rewet value.

Five new pre-weighed filter papers are then placed on the absorbent core in a similar manner, and the weight is placed on top of them for 30 seconds as before. The weight is removed and the second batch of filter papers are weighed. The difference in filter paper weight is the second rewet value.

The procedure is repeated one more time to determine the third rewet value.

The total rewet is the sum of the three individual rewet values, i.e.:

Total rewet=first rewet+second rewet+third rewet.

What is claimed is:

1. An absorbent core comprising:

a first structure comprising an upper layer comprising a first fibrous material having a wet compressibility of at least 5 cm$^3$/g and a drip capacity of a least 10 cm$^3$/g, the structure also comprising a first superabsorbent material having a substantially non-decreasing dynamic swelling rate, and a second structure positioned below the first structure, the second structure comprising a second fibrous material and a second superabsorbent material having a dynamic swelling rate of at least 0.2 g/g/sec and an absorption against pressure of at least 15 g/g at 50 g/cm$^2$ (0.7 psi), wherein the dynamic swelling rate of the first superabsorbent material is not greater than ⅔ of the dynamic swelling rate of the second superabsorbent material and wherein the absorbent core has a Total Rewet of not more than about 0.6 grams synthetic urine.

2. The absorbent core according to claim 1 wherein the first structure comprises an upper layer comprising the first fibrous material and a distinct layer comprising the first superabsorbent material, and the second structure comprises a layer comprising the second fibrous material and a distinct layer comprising the second superabsorbent material.

3. The absorbent core accordilig to claim 2 wherein each layer containing superabsorbent material consists essentially of superabsorbent material.

4. The absorbent core according to claim 1 wherein the dynamic swelling rate of the first superabsorbent material is not greater than ⅓ of the dynamic swelling rate of the second superabsorbent material.

5. The absorbent core according to claim 1 wherein the absorption pressure of the second superabsorbent material at 50 g/cm$^2$ (0.7 psi) is at least 20 g/g.

6. The absorbent core according to claim 1 wherein the first fibrous material comprises chemically cross-linked cellulosic fibres.

7. The absorbent core accordinig to claim 1 having an average theoretical basis capacity of at least 0.7 ml/cm$^2$ and an acquisition rate of at least 1.5 ml/sec at 50% of the theoretical basis capacity and a fluid uptake rate of at least 0.05 g/g/sec as measured by an X,Y-demand absorbency test.

8. The absorbent core according to claim 7 having a fluid uptake rate of at least 0.06 g/g/sec.

9. The absorbent core according to claim 7 having an average theoretical basis capacity of at least 0.8 ml/cm$^2$.

10. The absorbent core accordinig claim 1 having a stack height of not more than 9 mm as measured at 200 g/cm² (3 psi) in a stack height.

11. The absorbent core according to claim 1 wherein the first and/or second superabsorbent material is particulate.

12. The absorbent core according to claim 11 wherein the first superabsorbent is particulate and has a median mass particle size of more than 300 μm (50 mesh) and the second superabsorbent material is particulate and has a median mass particle size of less than 300 μm (50 mesh).

13. The absorbent core according to claim 12 wherein the first particulate superabsorbent material is in the range of 600 to 850 μm (20 to 30 mesh) and the second particulate superabsorbent material is in the range of 150 to 250 μm (60 to 100 mesh).

14. An absorbent article comprising
a liquid previous topsheet (2),
a liquid impervious backsheet (9), and
an absorbent core as defined in claim 1 and interposed between the topsheet and the backsheet with the first structure positioned towards the topsheet.

15. The article according to claim 14 and which is a disposable diaper, incontinence article or training pant.

* * * * *

UNITED STATES PATENT AND TRADEMARK OFFICE
CERTIFICATE OF CORRECTION

PATENT NO. : 5,762,641
DATED : June 9, 1998
INVENTOR(S) : Christopher Phillip Bewick-Sonntag et al.

It is certified that error appears in the above-identified patent and that said Letters Patent is hereby corrected as shown below:

Column 1,
Lines 14 and 16, delete "previous" and insert -- pervious --.

Column 3,
Line 20, delete "mold" and insert -- mould --.

Column 6,
Line 30, delete "AQUALIE CA®" and insert -- AQUALIC CA® --.
Line 31, delete "FAVOR SX®" and insert -- FAVDR SX® --.

Column 9,
Line 25, delete "previous" and insert -- pervious --.

Column 10,
Line 23, delete "previous" and insert -- pervious --.

Column 16,
Line 9, delete "sanmle" and insert -- sample --.

Column 22,
Line 45 delete "accordilig" and insert -- according --.
Line 58, delete "accordinig" and insert -- according Column 23,
Line 1, delete "accordinig" and insert -- according. --.

UNITED STATES PATENT AND TRADEMARK OFFICE
CERTIFICATE OF CORRECTION

PATENT NO. : 5,762,641
DATED : June 9, 1998
INVENTOR(S) : Christopher Phillip Bewick-Sonntag et al.

It is certified that error appears in the above-identified patent and that said Letters Patent is hereby corrected as shown below:

<u>Column 24,</u>
Line 6, delete "previous" and insert -- pervious --.

Signed and Sealed this

Fourteenth Day of March, 2006

JON W. DUDAS
*Director of the United States Patent and Trademark Office*